United States Patent
Liu et al.

(10) Patent No.: US 10,702,301 B2
(45) Date of Patent: Jul. 7, 2020

(54) CIRCUMCISION APPARATUS

(71) Applicants: Quancheng Liu, Changsha (CN); Fangxi Liu, Changsha (CN)

(72) Inventors: Quancheng Liu, Changsha (CN); Fangxi Liu, Changsha (CN)

(*) Notice: Subject to any disclaimer, the term of this patent is extended or adjusted under 35 U.S.C. 154(b) by 300 days.

(21) Appl. No.: 15/737,197

(22) PCT Filed: Jun. 3, 2016

(86) PCT No.: PCT/CN2016/084717
§ 371 (c)(1),
(2) Date: Dec. 15, 2017

(87) PCT Pub. No.: WO2016/202182
PCT Pub. Date: Dec. 22, 2016

(65) Prior Publication Data
US 2018/0185047 A1    Jul. 5, 2018

(30) Foreign Application Priority Data
Jun. 16, 2015 (CN) .......................... 2015 1 0333023

(51) Int. Cl.
*A61B 17/326* (2006.01)
*A61B 17/3209* (2006.01)

(52) U.S. Cl.
CPC ...... *A61B 17/326* (2013.01); *A61B 17/32093* (2013.01)

(58) Field of Classification Search
CPC .......................... A61B 17/326; A61B 17/32093
See application file for complete search history.

(56) References Cited

U.S. PATENT DOCUMENTS

| 2,238,660 A | 4/1941 | Santora |
| 2,296,594 A | 9/1942 | Blais et al. |
| (Continued) | | |

FOREIGN PATENT DOCUMENTS

| CN | 2403373 Y | 11/2000 |
| CN | 103340672 A | 10/2013 |
| (Continued) | | |

OTHER PUBLICATIONS

Chinese Office Action for corresponding Chinese patent application No. 201510333023.9, 8 pages.
(Continued)

*Primary Examiner* — Sarah W Aleman
(74) *Attorney, Agent, or Firm* — Calfee, Halter & Griswold LLP

(57) ABSTRACT

A circumcision apparatus includes a fixed support; a first through hole and a second through hole are machined on the fixed support along a same axial line; a knife rack shaft is penetrated through the first through hole; the first end of the knife rack shaft is connected with a locking mechanism to lock and position the knife rack shaft on the fixed support, the second end of the knife rack shaft is connected with a protective cover; the protective cover is extended to the exterior of the fixed support via the second through hole; the protective cover and the knife rack shaft are coaxial in detachable connection; a positioning sleeve in clearance fit with the protective cover is arranged at the second through hole; the positioning sleeve and the fixed support are in the detachable connection; and a space between the positioning sleeve and the protective cover is adaptive.

7 Claims, 2 Drawing Sheets

(56) References Cited

U.S. PATENT DOCUMENTS

| | | | |
|---|---|---|---|
| 2,471,864 A | | 5/1949 | De Palo |
| 3,473,533 A | * | 10/1969 | Freda .................. A61B 17/326 |
| | | | 606/118 |
| 3,874,389 A | * | 4/1975 | Baumgarten ........ A61B 17/326 |
| | | | 606/118 |
| 4,157,086 A | * | 6/1979 | Maiorano ........ A61B 17/32093 |
| | | | 600/369 |
| 5,817,117 A | | 10/1998 | Cartaxo |
| 2004/0215210 A1 | * | 10/2004 | Duel .................. A61B 17/326 |
| | | | 606/118 |
| 2012/0078265 A1 | | 3/2012 | Kostrzewski |

FOREIGN PATENT DOCUMENTS

| | | |
|---|---|---|
| CN | 103750886 A | 4/2014 |
| CN | 204246208 U | 4/2015 |
| CN | 104887296 A | 9/2015 |
| CN | 204839673 U | 12/2015 |
| JP | 61-8807 | 6/1986 |
| JP | 62-13608 | 4/1987 |
| WO | 2009091235 A2 | 7/2009 |

OTHER PUBLICATIONS

Chinese Office Action for corresponding Chinese patent application No. 201510333023.9, 9 pages.
Chinese Office Action for corresponding Chinese patent application No. 201510333023.9, 5 pages.
Search Report for International Application No. PCT/CN2016/084717 dated Sep. 8, 2016.

* cited by examiner

CIRCUMCISION APPARATUS

CROSS-REFERENCE TO RELATED APPLICATIONS

This application is the U.S. national stage entry of International Application No. PCT/CN2016/084717, filed Jun. 3, 2016, which claims priority to and the benefit of Chinese Patent Application No. 201510333023.9, filed on Jun. 16, 2015, the entire contents of which are incorporated herein by reference.

TECHNICAL FIELD

The present invention relates to the field of medical apparatuses, and particularly, to a circumcision apparatus.

BACKGROUND

The foreskin of a penis is a surplus skin, is positioned near a remote end of the penis and is also referred to as a penis foreskin. The foreskin substantially covers a head of the penis and is also referred to as a penis glans, a penis head or a glans for short. The circumcision is a surgical operation through which the foreskin of the penis is removed in part or in whole. The circumcision for the male is one of the most common operations in the world and has been performed due to a ceremony and a health reason since ancient times. Today, it may be performed due to a clinical reason or may be practiced to obey a religion or a culture (also referred to as a non-therapeutic circumcision). Generally, the non-therapeutic circumcision is performed by a practitioner and a non-clinical doctor in a religious or cultural group. About one-third of men throughout the world receive the circumcision in some time in life. In general, the circumcision is performed immediately after birth, or is performed during childhood or adolescence or occasionally on the youth (that is, after a dozen years).

At present, the foreskin is generally incised using a laser or mechanical direct incising method. In such a way, the foreskin incision is not smooth and complete; moreover, the bleeding amount is large, the operation time is long and the postoperative recovery is not easy. Therefore, there emerges a circumcision apparatus on the market. Although the existing circumcision apparatus can incise an unnecessary foreskin at one time, it cannot be applied to all sizes of the penises due to a fixed size. Thus, a circumcision apparatus having different sizes replaced according to an actual situation of an operation is required.

SUMMARY

The present invention provides a circumcision apparatus, so as to solve the technical problem of limited compatibility of the existing circumcision apparatus.

The technical solutions adopted by the present invention are as follows.

A circumcision apparatus includes a fixed support configured to position; a first through hole and a second through hole are machined on the fixed support along a same axial line; a knife rack shaft is penetrated through the first through hole; the first end, positioned at the exterior of the fixed support, of the knife rack shaft is connected with a locking mechanism configured to lock and position the knife rack shaft on the fixed support, and the second end of the knife rack shaft is connected with a protective cover configured to coat a penis glans; the protective cover is extended to the exterior of the fixed support via the second through hole; the protective cover and the knife rack shaft are coaxial and are in detachable connection;

a positioning sleeve in clearance fit with the protective cover is arranged at the second through hole; the positioning sleeve and the fixed support are in the detachable connection; a space between the positioning sleeve and the protective cover is adaptive with the thickness of a foreskin, such that the foreskin is extended into the fixed support.

Further, the detachable connection is threaded connection, splined connection or clamped connection.

Further, the locking mechanism is an adjusting lock nut.

Further, the protective cover includes a connecting section configured to be in coaxial connection with the knife rack shaft and an accommodation cavity configured to accommodate the penis glans; the connecting section and the accommodation cavity are in transition connection via an inclined section; the caliber of the inclined section along a direction from the accommodation cavity to the connecting section is reduced gradually.

Further, the positioning sleeve is of an annular shape; an end portion, toward the exterior of the fixed support, of the positioning sleeve is provided with a convex ring whose outer diameter is increased; the convex ring is propped against the bottom of the fixed support; an end portion, toward the interior of the fixed support, of the positioning sleeve is provided with a sharp portion whose inner diameter is gradually increased; the sharp portion is matched with the inclined section and is configured to limit a to-be-incised foreskin.

Further, a rotary knife rack rotationally connected around the knife rack shaft is arranged on the knife rack shaft; an incision knife configured to incise the foreskin is arranged on the rotary knife rack; the incision knife is fixed on the rotary knife rack via a locking piece.

Further, a knife point of the incision knife is positioned at the junction of the inclined section and the sharp portion.

Further, an elastic piece configured to apply a pretightening force to the rotary knife rack is arranged between the rotary knife rack and the fixed support.

Further, the rotary knife rack is connected with a drive mechanism configured to drive the rotary knife rack to automatically rotate, thereby automatically incising the foreskin.

Further, the drive mechanism includes a motor arranged on the fixed support; the motor outputs a power via a transmission shaft; the transmission shaft is stretched into the fixed support; and the transmission shaft is in linkage connection with the rotary knife rack in the fixed support.

The present invention has the following beneficial effects.

According to the circumcision apparatus disclosed by the present invention, through arranging the protective cover which is coaxial and is in the detachable connection with the knife rack shaft on the knife rack shaft, and arranging the positioning sleeve which is in the detachable connection with the fixed support at the second through hole of the fixed support, by replacing different sizes of the protective covers and the positioning sleeves, the circumcision apparatus disclosed by the present invention can be applied to different sizes of penises; and thus, the circumcision may be performed on the different sizes of the penises by the same circumcision apparatus, the scope of application is wide, and the operation is simple, convenient, time-saving and labor-saving.

Besides the above purposes, characteristics and advantages, other purposes, characteristics and advantages of the present invention will be described below in detail with reference to accompanying drawings.

BRIEF DESCRIPTION OF THE DRAWINGS

The accompanying drawings are described here to provide further understanding of the present invention, and form a part of the present invention. The schematic embodiments and description of the present invention are adopted to explain the present invention, and do not form improper limits to the present invention. In the drawings.

Figure 1:
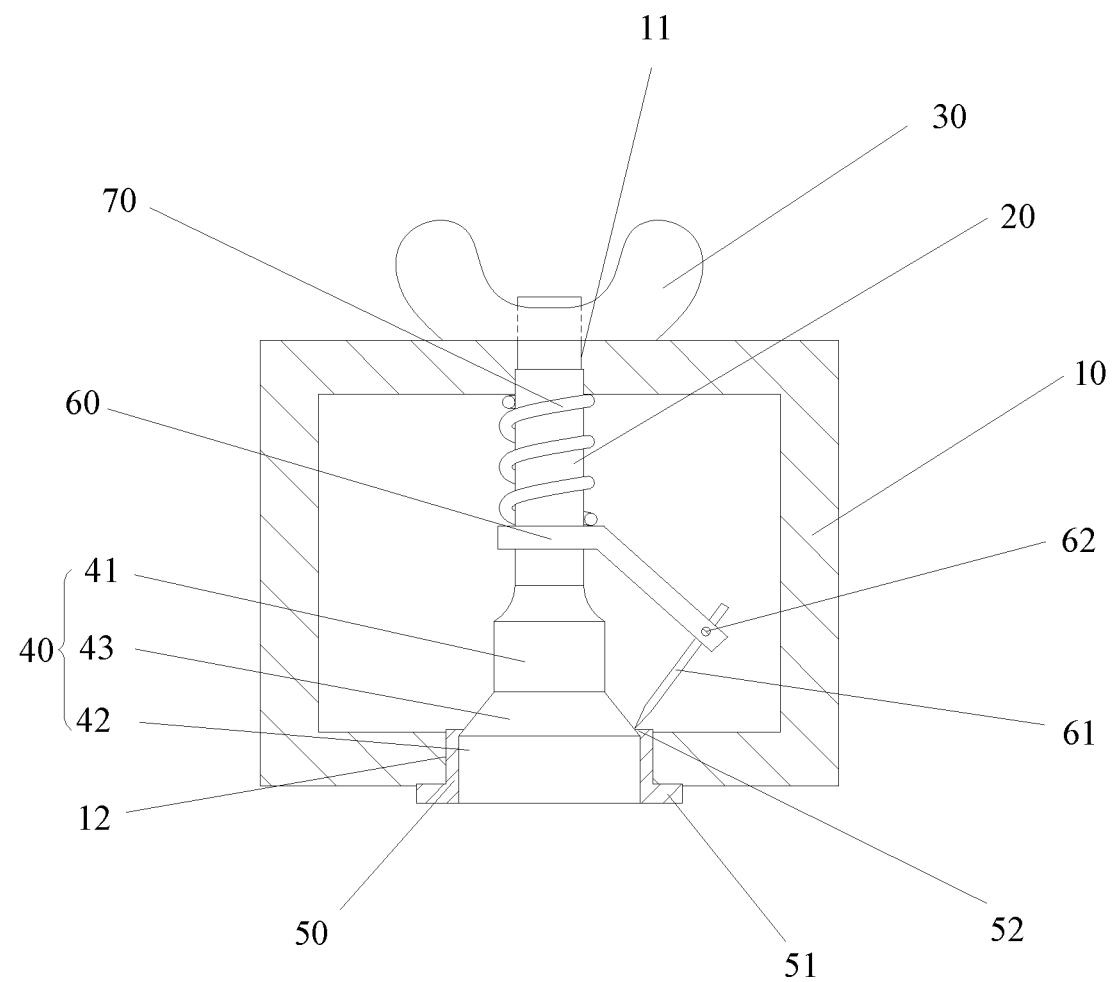
FIG. 1 is a structure diagram of a circumcision apparatus in a first preferred embodiment of the present invention.

Reference numbers in the drawings:

10. a fixed support; 11. a first through hole; 12. a second through hole; 20. a knife rack shaft; 30. a locking mechanism; 40. a protective cover; 41. a connecting section; 42. an accommodation cavity; 43. an inclined section; 50. a positioning sleeve; 51. a convex ring; 52. a sharp portion; 60. a rotary knife rack; 61. an incision knife; 62. a locking piece; 70. an elastic piece; 80. a motor; 81. a transmission shaft; 82. a drive gear.

DETAILED DESCRIPTION OF THE EMBODIMENTS

Hereinafter, the embodiments of the present invention will be described in detail with reference to the accompanying drawings. However, the present invention may be implemented in various different manners defined and covered in appended claims.

Embodiment 1

A preferred embodiment of the present invention provides a circumcision apparatus. The circumcision apparatus in this embodiment may perform a circumcision on different sizes of penises, the scope of application is wide and the practicability is huge. Specifically, referring to FIG. 1, the circumcision apparatus in this embodiment includes a fixed support 10 configured to position; a first through hole 11 and a second through hole 12 are machined on the fixed support 10 along a same axial line; a knife rack shaft 20 is penetrated through the first through hole 11; the first end, positioned at the exterior of the fixed support 10, of the knife rack shaft 20 is connected with a locking mechanism 30 configured to lock and position the knife rack shaft 20 on the fixed support 10, and the second end of the knife rack shaft 20 is connected with a protective cover 40 configured to coat a penis glans; the protective cover 40 is extended to the exterior of the fixed support 10 via the second through hole 12; the protective cover 40 and the knife rack shaft 20 are coaxial and are in detachable connection; a positioning sleeve 50 in clearance fit with the protective cover 40 is arranged at the second through hole 12; the positioning sleeve 50 and the fixed support 10 are in the detachable connection; and a space between the positioning sleeve 50 and the protective cover 40 is adaptive with the thickness of a foreskin, such that the foreskin is extended into the fixed support 10.

In work, the protective cover 40 and the positioning sleeve 50 that are matched are selected. The protective cover 40 is mounted on the knife rack shaft 20. The positioning sleeve 50 is mounted to the second through hole 12. Through adjusting a distance of the knife rack shaft 20 along an axial direction, the protective cover 40 coats a to-be-operated penis glans. And the foreskin of the penis is extended into the fixed support 10 via the space between the protective cover 40 and the positioning sleeve 50 and is positioned, thereby making preparations for the subsequent circumcision.

According to the circumcision apparatus in the embodiment, through arranging the protective cover 40 which is coaxial and is in the detachable connection with the knife rack shaft 20 on the knife rack shaft 20, and arranging the positioning sleeve 50 which is in the detachable connection with the fixed support 10 at the second through hole 12 of the fixed support 10, by replacing different sizes of the protective covers 40 and the positioning sleeves 50, the circumcision apparatus disclosed by the present invention can be applied to different sizes of penises; and thus, the circumcision may be performed on the different sizes of the penises by the same circumcision apparatus, the scope of application is wide, and the operation is simple and convenient. In the embodiment, since the protective cover 40 and the knife rack shaft 20 are coaxially arranged, and the matching position between the protective cover 40 and the penis glans is adjusted via an end portion, extended out of the fixed support 10, of the knife rack shaft 20, the adjustment is convenient. The knife rack shaft 20 is fixed on the fixed support 10 via the locking mechanism 30, so the incision error due to position shaking during the operation is avoided. Further, with the reasonable space between the positioning sleeve 50 and the protective cover 40, the positioning accuracy in circumcision is further improved; and the positioning sleeve 50 takes a hemostasis effect for protection of the incision.

In the embodiment, the detachable connection is threaded connection, splined connection or clamped connection. For example, between the protective cover 40 and the knife rack shaft 20, the positioning sleeve 50 is in the threaded connection, the splined connection or the clamped connection at the second through hole 12 of the fixed support 10, so as to quickly replace the corresponding size of the protective cover 40 and the positioning sleeve 50 and to meet the requirements of different sizes of the penises (both adults and kids) on the circumcision.

In the embodiment, the locking mechanism 30 is an adjusting lock nut. After the knife rack shaft 20 is adjusted to an appropriate position, it is fixed on the fixed support 10 through the adjusting lock nut, such that the protective cover 20 is stably positioned.

In the embodiment, preferably, the protective cover 40 includes a connecting section 41 configured to be in coaxial connection with the knife rack shaft 20 and an accommodation cavity 42 configured to accommodate the penis glans; the connecting section 41 and the accommodation cavity 42 are in transition connection via an inclined section 43; the caliber of the inclined section 43 along a direction from the accommodation cavity 42 to the connecting section 41 is reduced gradually. In the embodiment, through the inclined section 43 whose caliber is gradually reduced along the accommodation cavity 42 to the connecting section 41, the foreskin may be positioned better, such that the edge of the foreskin is attached to the inclined section 43, and the inclination of the incision in circumcision is avoided.

In the embodiment, preferably, the positioning sleeve 50 is of an annular shape; an end portion, toward the exterior of the fixed support 10, of the positioning sleeve 50 is provided with a convex ring 51 whose outer diameter is increased; the convex ring 51 is propped against the bottom of the fixed support 10; an end portion, toward the interior of the fixed support 10, of the positioning sleeve 50 is provided with a sharp portion 52 whose inner diameter is gradually increased; the sharp portion 52 is matched with the inclined section 43 and is configured to limit a to-be-incised foreskin. In the embodiment, through the matching between the sharp portion 52 and the inclined section 43, the to-be-incised foreskin may be accurately positioned, such that the incision is guaranteed to be smooth and is not inclined.

Preferably, in order to perform the circumcision conveniently, a rotary knife rack 60 rotationally connected around the knife rack shaft 20 is arranged on the knife rack shaft 20 in the embodiment, alternatively; an incision knife 61 configured to incise the foreskin is arranged on the rotary knife rack 60; the incision knife 61 is fixed on the rotary knife rack 60 via a locking piece 62. Preferably, a knife point of the incision knife 61 is positioned at the junction of the inclined section 43 and the sharp portion 52. By employing the incision knife 61 having such structure for the circumcision, a front end of the foreskin is coated at the inclined section 43 and an outer edge thereof is propped against by the sharp portion 52. As a result, not only can the positioning accuracy of the circumcision be guaranteed well, but the foreskin incision also can be pressed tightly by the sharp portion, taking the intra-operative and post-operative hemostasis effect well.

Preferably, an elastic piece 70 configured to apply a pretightening force to the rotary knife rack 60 is arranged between the rotary knife rack 60 and the fixed support 10. In the embodiment, the elastic piece 70 is a spring. Through arranging the spring to apply a downward acting force to the rotary knife rack 60, the incision operation is simple, convenient and reliable.

Embodiment 2

Figure 2:
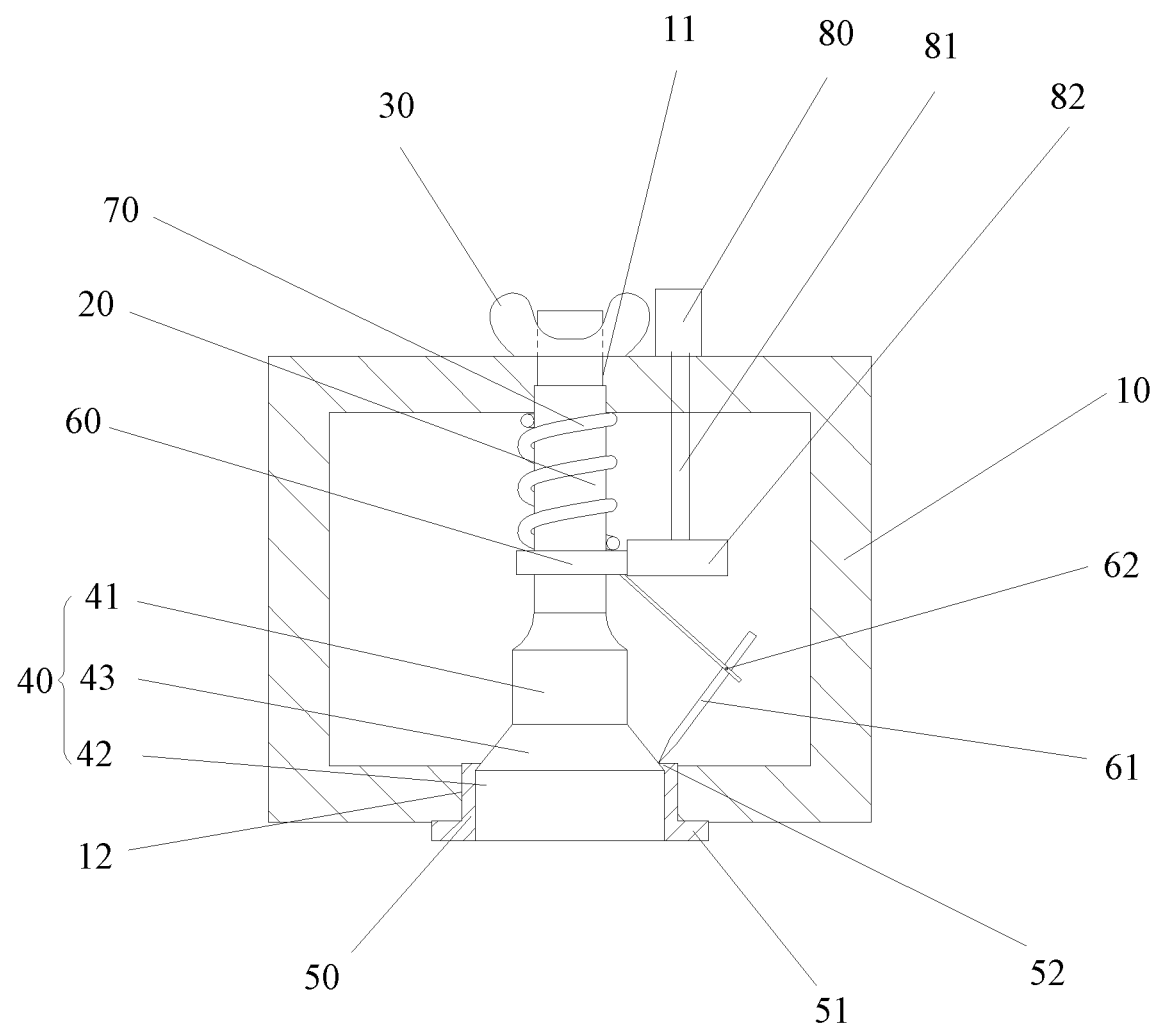
FIG. 2 is a structure diagram of a circumcision apparatus in a second preferred embodiment of the present invention.

FIG. 2 is a structure diagram of a circumcision apparatus in a second preferred embodiment of the present invention. Referring to FIG. 2, based on the first embodiment, there increases a drive mechanism for driving the rotary knife rack 60 to automatically rotate, thus driving the incision knife 61 to automatically incise the foreskin in the second embodiment.

In the embodiment, the drive mechanism comprises a motor 80 arranged on the fixed support 10; the motor 80 outputs a power via a transmission shaft 81; the transmission shaft 81 is stretched into the fixed support 10; and the transmission shaft 81 is in linkage connection with the rotary knife rack 60 in the fixed support 10. Specifically, an end portion, positioned in the fixed support 10, of the transmission shaft 81 is connected with a drive gear 82; the drive gear 82 is matched with an outer peripheral gear of the rotary knife rack 60. Under the dynamic action of the motor 80, the transmission shaft 81 drives the drive gear 82, thereby driving the rotary knife rack 60 to rotate around the knife rack shaft 20 and thus implementing the circumcision of the incision knife 61 fixedly arranged on the rotary knife rack 60. In the embodiment, by virtue of the action of the drive mechanism to the rotary knife rack 60, the automatic control on the circumcision is implemented, and the operation is simple and convenient.

The above only are preferable embodiments of the present invention and are not intended to limit the present invention. A person skilled in the art may make various modifications and changes to the present invention. Any modification, equivalent replacement and improvement made within the spirit and the principle of the present invention shall fall within the scope of protection of the present invention.

What is claimed is:

1. A circumcision apparatus, comprising:
   a fixed support,
   a first through hole and a second through hole, disposed on the fixed support along a same axial line,
   a knife rack shaft penetrating through the first through hole, wherein a first end of the knife rack shaft is positioned at an exterior of the fixed support and is connected with a locking mechanism, the locking mechanism selectively locks and positions the knife rack shaft on the fixed support, a second end of the knife rack shaft is connected with a protective cover, the protective cover selectively covers a penis glans; the protective cover is extended to the exterior of the fixed support via the second through hole; the protective cover and the knife rack shaft are coaxial and have a first detachable connection,
   a positioning sleeve, being in clearance fit with the protective cover and disposed at the second through hole, wherein the positioning sleeve and the fixed support have a second detachable connection; a space between the positioning sleeve and the protective cover is adjustable according to a thickness of a foreskin, such that the foreskin is extendable into the fixed support,
   a rotary knife rack, disposed on the knife rack shaft and rotationally connected around the knife rack shaft, and
   an incision knife, selectively incising the foreskin and disposed on the rotary knife rack, wherein the incision knife is fixed on the rotary knife rack via a locking piece,
   wherein the rotary knife rack is connected with a drive mechanism, the drive mechanism selectively drives the rotary knife rack to automatically rotate, thereby automatically incising the foreskin,
   wherein the drive mechanism comprises a motor arranged on the fixed support; the motor outputs a power via a transmission shaft; the transmission shaft extends into the fixed support; and the transmission shaft is in linkage connection with the rotary knife rack in the fixed support.

2. The circumcision apparatus according to claim 1, wherein the first and second detachable connections are a threaded connection, a splined connection or a clamped connection.

3. The circumcision apparatus according to claim 1, wherein the locking mechanism is an adjusting lock nut.

4. The circumcision apparatus according to claim 1, wherein the protective cover comprises:
   a connecting section, configured to be in a coaxial connection with the knife rack shaft and an accommodation cavity, configured to accommodate the penis glans,
   wherein the connecting section and the accommodation cavity are in transition connection via an inclined section; the caliber of the inclined section along a direction from the accommodation cavity to the connecting section is reduced gradually.

5. The circumcision apparatus according to claim 4, wherein the positioning sleeve is of an annular shape, a first end portion of the positioning sleeve extends toward the exterior of the fixed support and comprises a convex ring with an increased outer diameter, the convex ring is propped against a bottom of the fixed support, a second end portion of the positioning sleeve extends toward an interior of the fixed support and comprises a sharp portion with a decreased inner diameter in the direction toward the interior of the fixed support, the sharp portion is matched with the inclined section and selectively limits a to-be-incised foreskin.

6. The circumcision apparatus according to claim 1, wherein a knife point of the incision knife is positioned at the junction of the inclined section and the sharp portion.

7. The circumcision apparatus according to claim 6 further comprises: an elastic piece, disposed between the rotary knife rack and the fixed support that selectively applies a pretightening force to the rotary knife rack.

\* \* \* \* \*